(12) United States Patent
Lyons

(10) Patent No.: US 8,333,202 B2
(45) Date of Patent: Dec. 18, 2012

(54) ADJUSTABLE DENTAL DEVICE FOR TREATMENT OF SLEEP APNEA AND SNORING

(75) Inventor: Donald Richard Lyons, Annapolis, MD (US)

(73) Assignee: Donald R. Lyons, Jr., Annaplois, MD (US)

( * ) Notice: Subject to any disclaimer, the term of this patent is extended or adjusted under 35 U.S.C. 154(b) by 186 days.

(21) Appl. No.: 12/661,714

(22) Filed: Mar. 23, 2010

(65) Prior Publication Data
US 2010/0242969 A1   Sep. 30, 2010

Related U.S. Application Data

(60) Provisional application No. 61/210,933, filed on Mar. 24, 2009.

(51) Int. Cl.
*A61C 5/14* (2006.01)
*A61C 3/00* (2006.01)

(52) U.S. Cl. ........ 128/848; 128/859; 128/860; 128/861; 128/862; 433/6; 433/7; 433/8

(58) Field of Classification Search ............. 128/201.26, 128/201.18, 204.18, 206.29, 207.11, 206.18, 128/206.21, 848, 859, 860, 861, 862; 602/902; 433/6–8
See application file for complete search history.

(56) References Cited

U.S. PATENT DOCUMENTS

| 5,823,193 | A  | * | 10/1998 | Singer et al. | 128/848 |
| 5,941,247 | A  | * | 8/1999 | Keane | 128/848 |
| 2006/0231101 | A1 | * | 10/2006 | Cannon | 128/206.29 |
| 2010/0218773 | A1 | * | 9/2010 | Thornton | 128/848 |

* cited by examiner

*Primary Examiner* — Patricia Bianco
*Assistant Examiner* — Nihir Patel

(57) ABSTRACT

An adjustable dental device for use with a CPAP system in the treatment of sleep apnea and snoring is comprised of an upper bite block, a lower bite block having one or more tongue retainers, means for adjustably connecting the upper bite block to the lower bite block, and means for connecting the dental device to a CPAP system. The adjustable dental device is compatible with a variety of CPAP systems, including systems that utilize nasal inserts and systems that utilize a nasal mask.

5 Claims, 9 Drawing Sheets

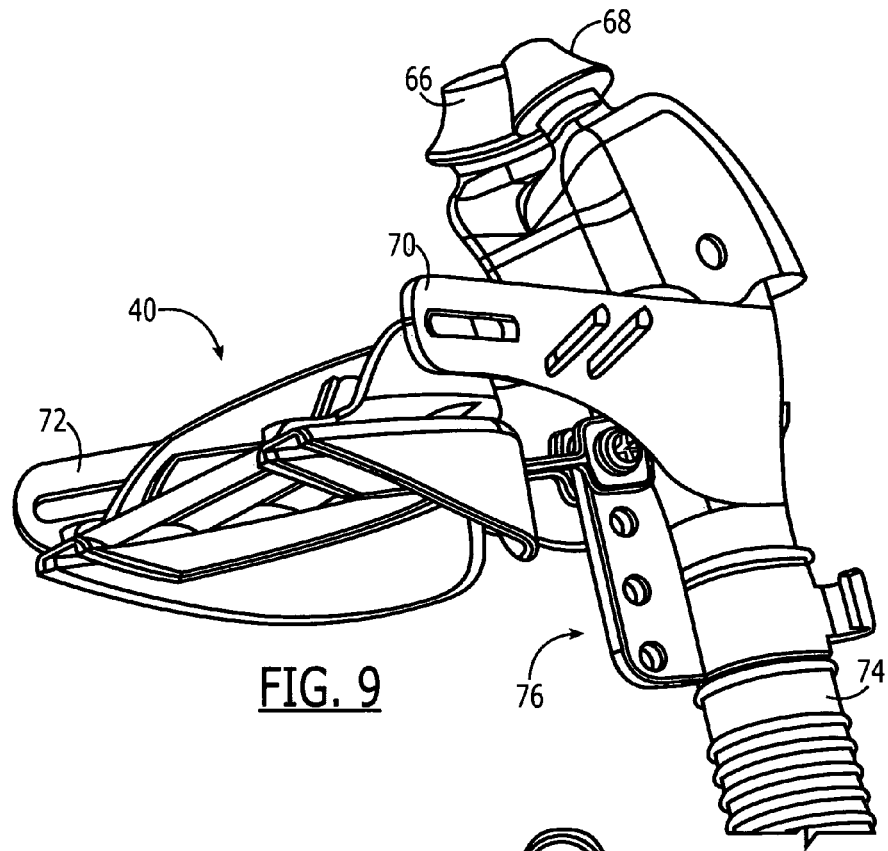
FIG. 9
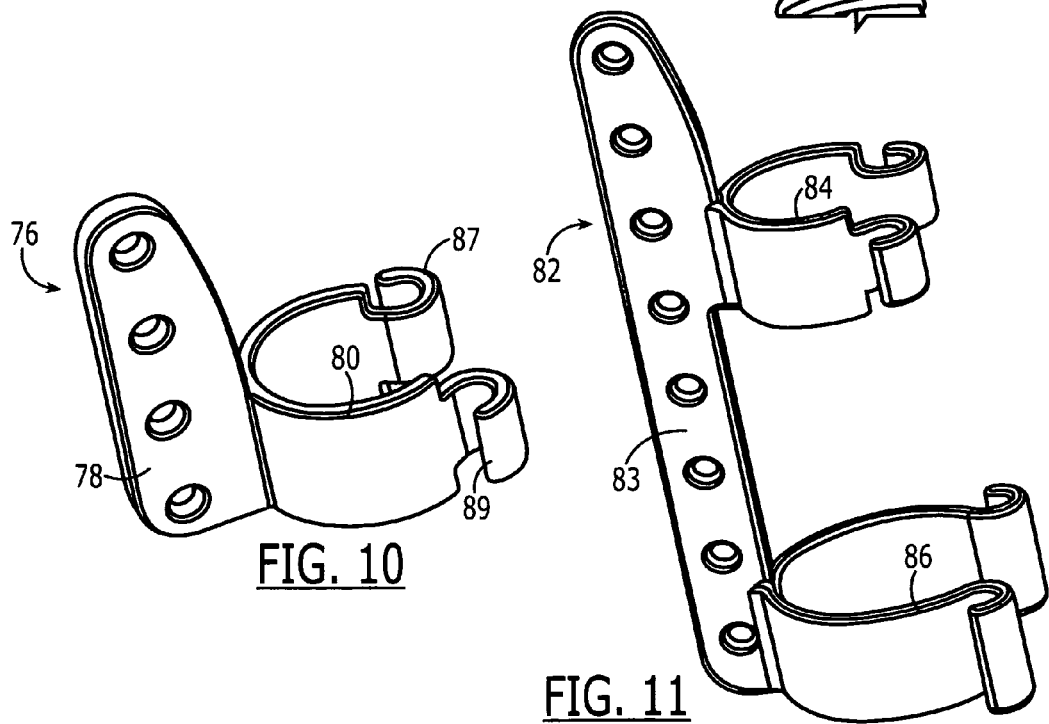
FIG. 10
FIG. 11

ADJUSTABLE DENTAL DEVICE FOR TREATMENT OF SLEEP APNEA AND SNORING

CLAIM OF PRIORITY

This patent application, and any patent(s) issuing therefrom, claims priority to U.S. provisional patent application No. 61/210,933, filed on Mar. 24, 2009, entitled "Adjustable dental device for treatment of sleep apnea and snoring", which is incorporated herein by reference in its entirety.

BACKGROUND OF THE INVENTION

Sleep apnea affects millions of Americans according to the National Institutes of Health. There are three types of apnea: obstructive, central, and mixed. Obstructive sleep apnea is the most common. The root cause of all three is the interruption of breathing during sleep, which occurs repeatedly, sometimes hundreds of times during the night.

A common treatment for obstructive sleep apnea is continuous positive airway pressure (herein referred to as "CPAP"). CPAP works through the use of a respirator device by blowing pressurized room air through the airway at a pressure high enough to keep the throat open. The pressure level is set according to the patient's needs. While CPAP is the most effective method currently for treating obstructive sleep apnea according to the American Sleep Apnea Association, there are many challenges and considerations involved in selection and use of the current CPAP interface devices. These include, by way of example, problems with the fit and comfort of the patient interface to the CPAP system. Such prior art interfaces are, in general, limited in adjustability or bulky and complicated. For example, many interfaces require head straps, which can be awkward, create patient anxiety, and otherwise interfere with patient comfort.

In treating sleep apnea and snoring with or without a CPAP system, a well known practice is to provide a means to maintain the lower jaw or mandible in an anterior, protruded position relative to the upper arch or maxilla. This is typically achieved through the use of a dental device of some sort. In designing such dental devices, one must consider the fact that both teeth and dental arches vary significantly across the patient population in terms of size and spacing. Furthermore, most people have some degree of malocclusion, which is defined herein as a misalignment of the teeth, or the incorrect relation between the teeth of the two dental arches, or a combination thereof.

Accordingly, adjustability for a wide range of malocclusion is advantageous as a feature of a dental device for treating sleep apnea and snoring. So too is a means to provide a comfortable resting place for the tongue which retains the tongue in a proper position to promote an open airway while remaining comfortable for several hours while sleeping.

SUMMARY

An adjustable dental device for use with a CPAP system in the treatment of sleep apnea and snoring is comprised of an upper bite block, a lower bite block having one or more tongue retainers, means for adjustably connecting the upper bite block to the lower bite block, and means for connecting the dental device to a CPAP system. The adjustable dental device is compatible with a variety of CPAP systems, including systems that utilize nasal inserts and systems that utilize a nasal mask.

One object of the present invention to improve upon the current CPAP interface devices for better fit, comfort, and ease of use. It is another object of this invention to provide an interface for securing various CPAP devices with reduced need for head straps, which can be awkward in use, create anxiety, and otherwise interfere with patient comfort. It is another object of this invention to provide for an improve bite fit when molding a dental device, including means for providing a wide range of adjustability for malocclusion.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 9 is a perspective view illustrating a dental device mount for attaching one embodiment of an adjustable dental device to a respiratory having head strap attachments.

FIG. 10 illustrates further details of the dental device mount shown in FIG. 9.

FIG. 11 illustrates an alternative embodiment of a dental device mount having two attachment clips.

DETAILED DESCRIPTION OF THE INVENTION

Figure 1:
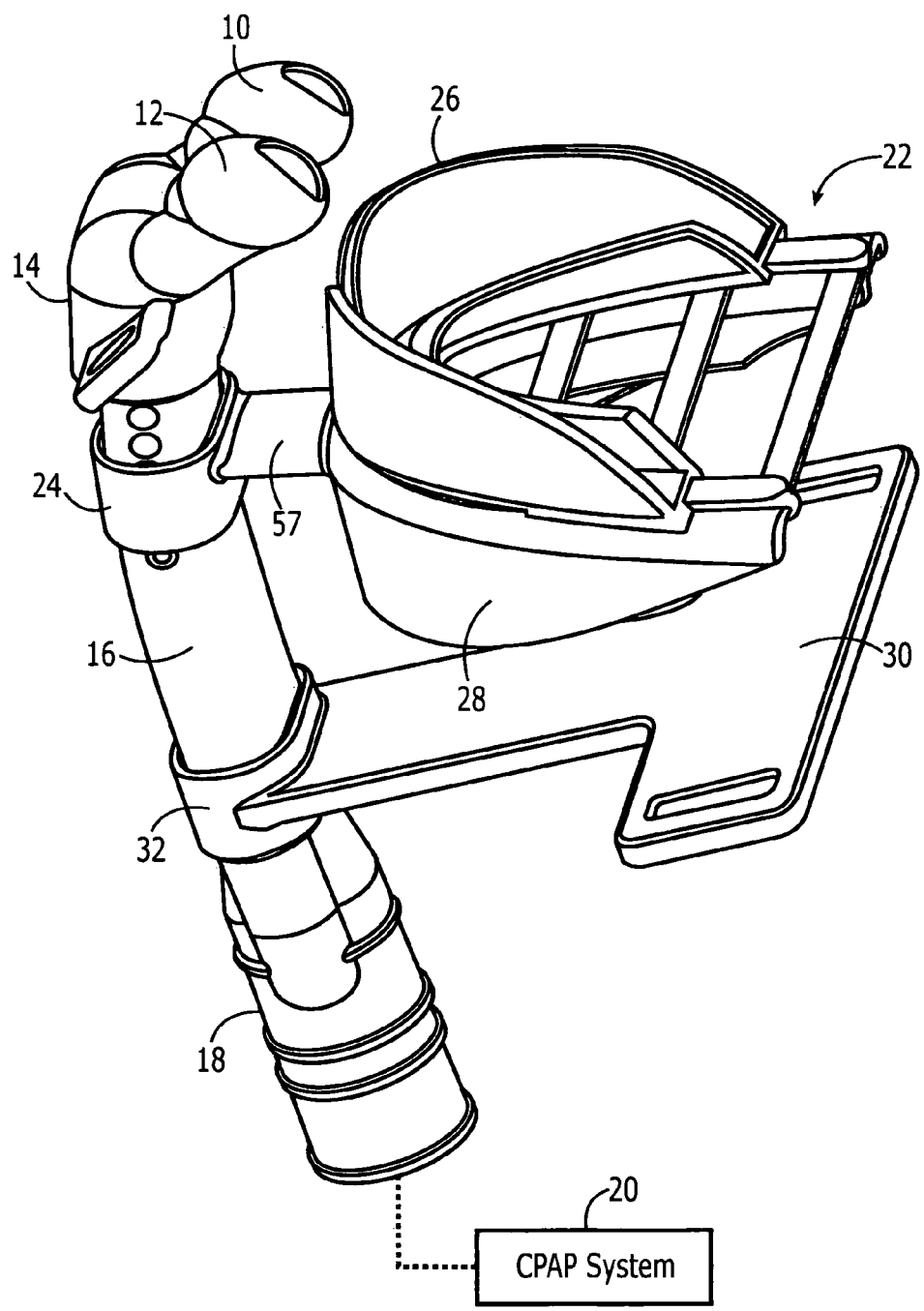
FIG. 1 illustrates an adjustable dental device for treatment of sleep apnea and snoring according to the teachings of the present invention.

FIG. 1 illustrates one embodiment of an adjustable dental device for treatment of sleep apnea and snoring according to the teachings of the present invention. As shown in FIG. 1, nasal inserts 10, 12 are provided for fitting in a patient's nostrils. Such nasal inserts 10, 12 are also referred to as nasal pillows or nasal buds. The particular nasal inserts 10, 12 shown in FIG. 1 are illustrative only, and any other nasal inserts, nasal buds, nasal pillows, or nasal masks may be used without departing from the intended scope of the present invention.

In this embodiment, nasal inserts 10, 12 are coupled through interaction assembly 14, upper air tube 16, and lower air tube 18 to CPAP system 20. CPAP system 20, illustrated here as a block symbol to represent its functionality as opposed to physical appearance, provides constant positive air pressure to the patient through nasal inserts 10, 12. The pressure of the air delivered by CPAP system 20 depends upon the severity of the breathing disorder being treated. The more severe the disorder, the greater the pressure must be. In general, increasing the air pressure delivered by CPAP system 20 increases the opening of the breathing passageway. CPAP system 20 is shown as an example only. Other systems for delivering air at constant or varying pressures also may be used. Furthermore, CPAP system 20 may deliver any breathable gas, such as air, pure oxygen, or a mixed gas containing oxygen and an inert gas such as nitrogen, helium, or the like. It should be understood that the term "air" used throughout this patent is meant to include any breathable gas.

As shown in FIG. 1, adjustable dental device 22 is connected to upper air tube 16 by attachment member 57 and dental device connector 24. Adjustable dental device 22 includes upper bite block 26 and lower bite block 28. Interaction assembly 14 is configured so as to allow air exhaled by the patient through nasal inserts 10, 12 to be exhausted out of interaction assembly 14 or upper air tube 16. This is preferably performed by providing small holes in interaction assembly 14 or upper air tube 16 through which exhaust air can be vented or by providing one or more one-way exhaust valves. If air holes are used, the total cross-sectional flow area is sufficiently small to prevent too much air loss from CPAP system 20 while being sufficiently large that no noticeable effort is needed by the patient to exhale. Interaction assembly 14 and nasal inserts 10, 12 are preferably made of hypoallergenic, transparent material. The body of interaction assembly 14 is substantially rigid to provide a stable platform for nasal inserts 10, 12 and a stable connection to upper air tube 16.

Chin stabilizer 30 is attached to upper air tube 16 by chin stabilizer connector 32. Chin stabilizer 30 is preferably a single piece of plastic. The plastic may be transparent to make the stabilizer inconspicuous. In operation, chin stabilizer 30 provides a cantilever type support, bracing the device through use of the patient's chin as a support surface.

Air tubes 16, 18 are preferably molded as a single piece of plastic. The plastic may be transparent to make the air tubes inconspicuous. While single piece construction is preferable, air tubes 16, 18 may be separate pieces and connected together in any suitable fashion. For example, upper air tube 16 may be inserted into lower air tube 18 and held in place through a compression fit or could be bonded through application of an adhesive or be applying heat to fuse tubes 16 and 18 together.

Interaction assembly 14 is removable from upper air tube 16 to allow dental device connector 24 and chin stabilizer connector 32 to slide over the exposed end of upper air tube 16 for mounting and removing connectors 24, 32. Interaction assembly 14, like air tubes 16, 18, is preferably made of transparent material to make the assembly inconspicuous.

As will be illustrated with reference to other illustrations below, the substantially cylindrical dental device connector 24 that is illustrated in FIG. 1 can be replaced with tabs for a nut-and-bolt type connection, or by a compression type fitting. Other connection means are readily used within the scope of the present invention and are well known by those of ordinary skill in the art.

Figure 2:
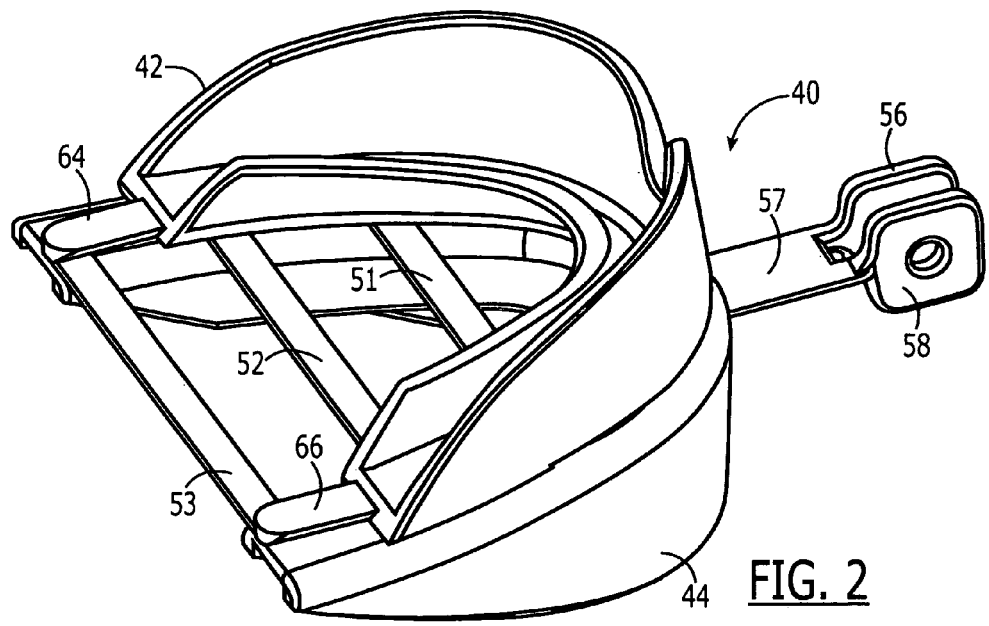
FIG. 2 is a perspective view of an adjustable dental device according to one embodiment of the present invention which can be used with a wide range of respirators.

FIG. 2 illustrates an adjustable dental device 40 in accordance with the teachings of the present invention which can be used with a wide range of CPAP interfaces. Adjustable dental device 40 as illustrated here is identical to adjustable dental device 22 of FIG. 1 with the exception of differences in connection means. The following detailed description of features of adjustable dental device 40 are therefore applicable to adjustable dental device 22 with the exception of the latter's use of connector 24.

Adjustable dental device 40 includes upper bite block 42 and lower bite block 44. Lower bite block 44 includes tongue retainers 51, 52, 53 and an alternative dental device connector means comprised of attachment member 57 and tabs 56, 58. Bite blocks 42, 44 are connected together by engaging sliding dovetails 64, 66 in corresponding dovetail grooves 68, 70 (not shown). This allows a patient to adjust the relative positions of bite blocks 42, 44 for custom fitting prior to thermal molding as described more fully below.

Bite blocks 42, 44 are made of a deformable material for forming a mold of the patient's teeth for proper fitting. A suitable deformable material is the ethylene-vinyl acetate copolymer resin sold under the registered trademark ELVAX. Any other suitable deformable material may also be used. To make a custom fit in accordance with the teachings of the present invention, a patient will join bite blocks 42, 44 by engaging sliding dovetails 64, 66 with dovetail grooves 68, 70 or an alternative connection means. The unheated dental device 40 is then placed into the patient's mouth. The patent then adjusts the relative position of bite blocks 42, 44 using the slidable feature of dovetails 64, 66 and grooves 68, 70 so that it closely matches the patient's occlusion. Groves 68, 70 provide a snug fit with dovetails 64, 66 respectively, thereby holding bite blocks 42, 44 in place. Having adjusted the relative position of bite blocks 42, 44 using the slidable feature of dovetails 64, 66 and grooves 68, 70, dental device 40 is then removed from the patient's mouth and heated to a temperature of about 150° F. using a microwave oven or by heating dental device 40 in hot water so as to place the material in its deformable state. The patient then inserts dental device 40 and bites down, thereby deforming bite blocks 42, 44 into the shape of the patient's teeth and deforming tongue retainers 51, 52, 53 to conform generally to the surface of the tongue. Mouthpiece 40 is then removed and allowed to cool, thereby setting the bite blocks 42, 44 into a mold of the patient's teeth and tongue retainers 51, 52, 53 to conform generally to the surface of the tongue. In addition, sliding dovetails 64, 66 are fused with dovetail grooves 68, 70 when cooled, thereby fixing bite blocks 42, 44 with the patient's occlusion.

Figure 3:
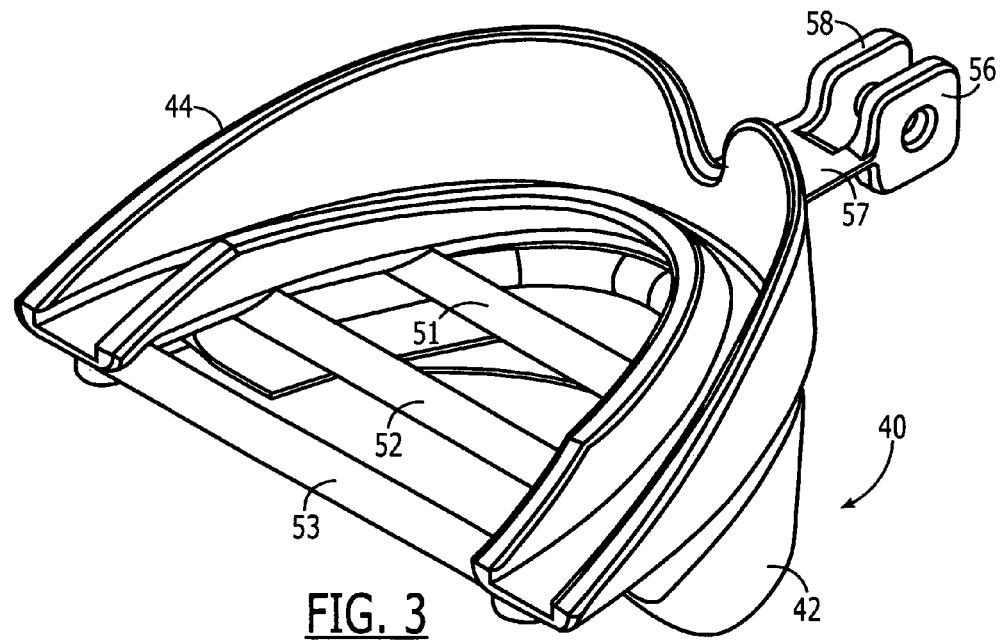
FIG. 3 is a perspective view of an adjustable dental device illustrating details of the bottom bite block.
Figure 3A:
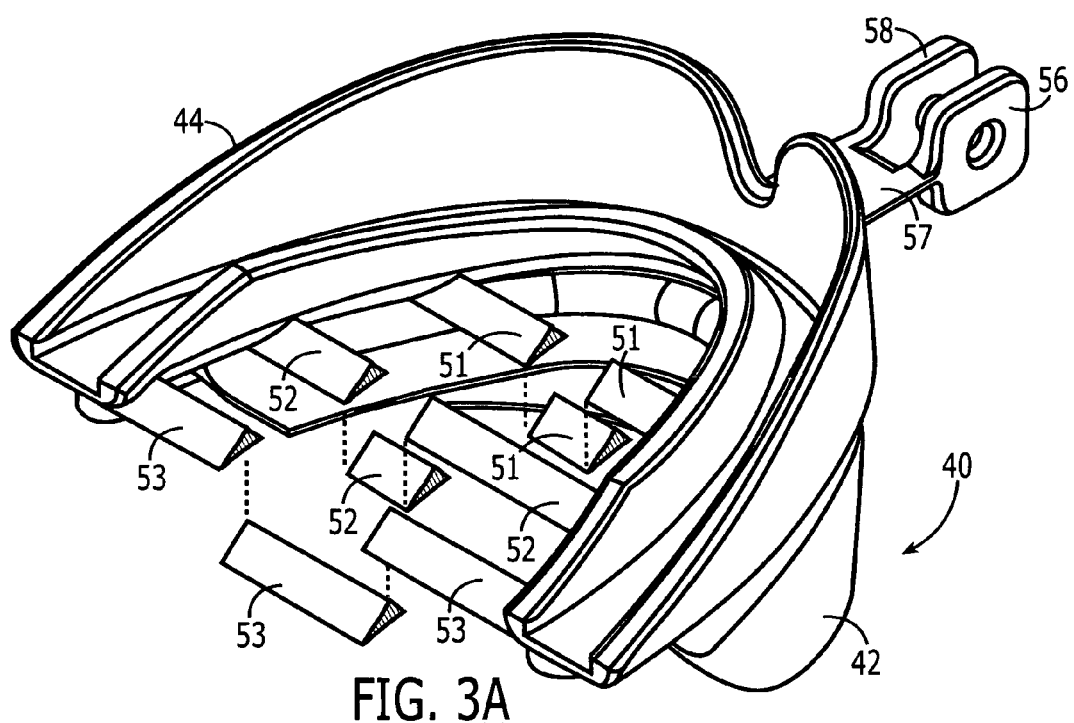
FIG. 3A is a perspective view of an adjustable dental device illustrating the triangular cross section of the tongue retainers.

FIG. 3 illustrates the tongue side of tongue retainers 51, 52, 53. As shown in FIG. 3, the cross-section of each of the tongue retainers 51, 52, 53 is preferably wedge shaped, as in an approximate 30-60-90 degree right triangle wherein the 60 degree angle is pointed substantially towards the tongue and the hypotenuse faces substantially towards the tongue in a posterior slant. This cross-sectional shape and orientation helps to prevent the tongue from slipping backwards into the throat during sleep. Further included in the preferred embodiment of this dental device is the attachment member 57 which extends from the front of dental device 40 and exits the patient's mouth. The attachment member 57 in this embodiment provides two vertically situated tabs 56, 58 with aligned holes through each tab. Mouthpiece 40, in this particular embodiment, is attached via a nut-and-bolt connection (not shown in this figure) inserted through the holes of tabs 56, 58 and through a corresponding hole present on a separate attachment device.

Figure 4:
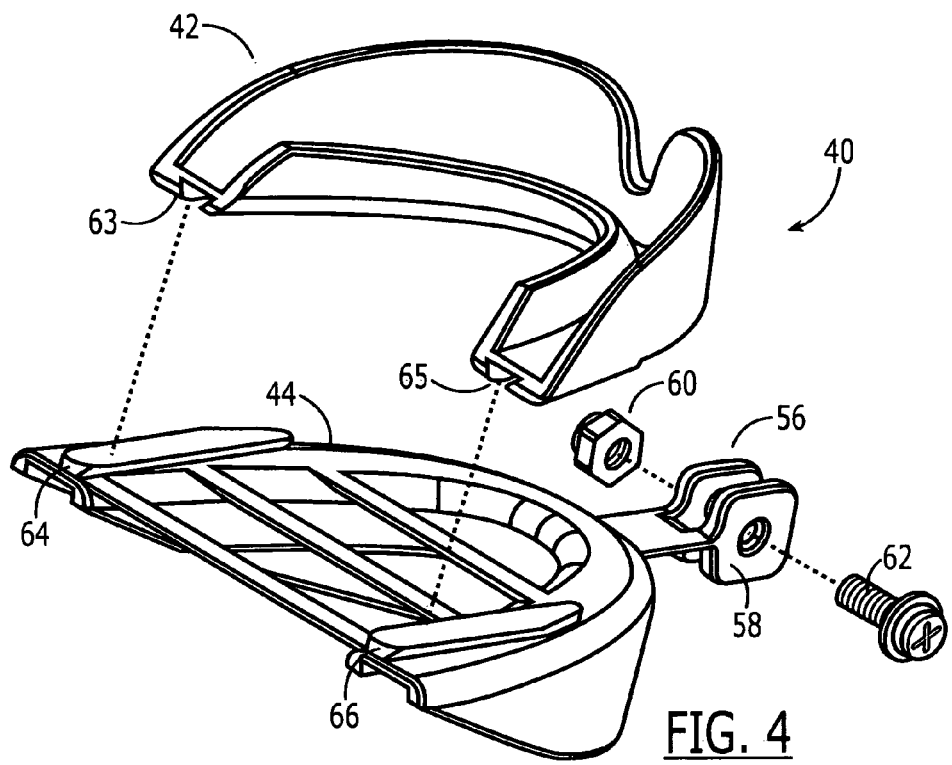
FIG. 4 is an exploded view of one embodiment of an adjustable dental device illustrating details of a connection means.

FIG. 4 is an exploded view of an adjustable dental device 40 illustrating bite blocks 42, 44, tabs 56, 58, nut 60, and bolt 62. Sliding dovetails 64, 66 and dovetail grooves 63, 65 are also shown in FIG. 4. Nut 60 and bolt 62 may be made of metal, plastic, or any other suitable material. A wing nut, clip, or other means may also be used in place of the nut-and-bolt connection illustrated here. Such connection means are well known in the art and are readily available.

Figure 5:
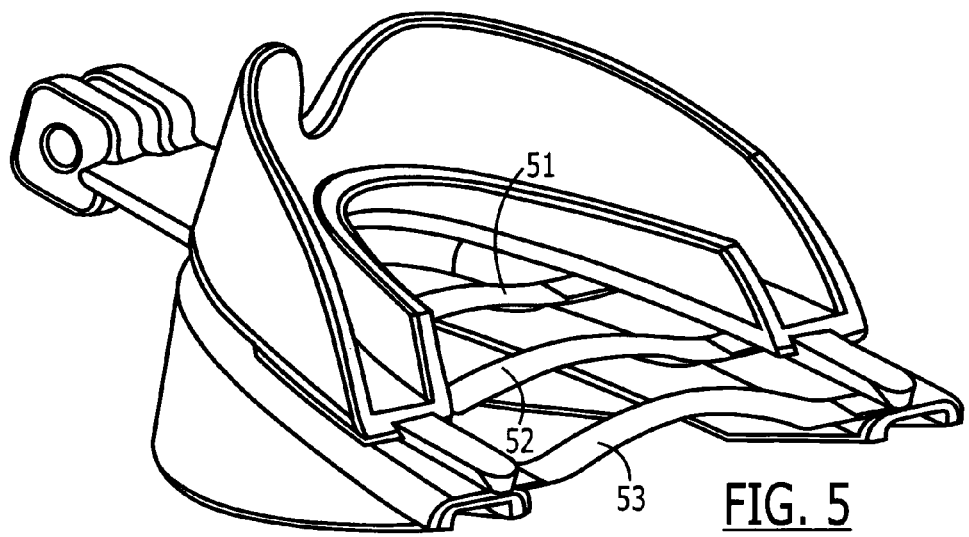
FIG. 5 is a perspective view of one embodiment of an adjustable dental device illustrating the deformation of tongue retainers after molding.

FIG. 5 is another perspective view of an adjustable dental device illustrating the deformation of tongue retainers 51, 52, 53 as they might appear after molding to a patient's mouth. This structure and functionality can be used for various embodiments of the adjustable dental device and independent on the particular CPAP system used. After molding, tongue retainers 51, 52, 53 are shaped to conform generally to the surface of the patient's tongue as the tongue rests naturally and comfortably against tongue retainers 51, 52, 53 with the molded dental device in the patient's mouth. Accordingly, the position of the tongue and lower jaw that are provided as a result of the present invention provide for improved airflow and reduced snoring.

Figure 6:
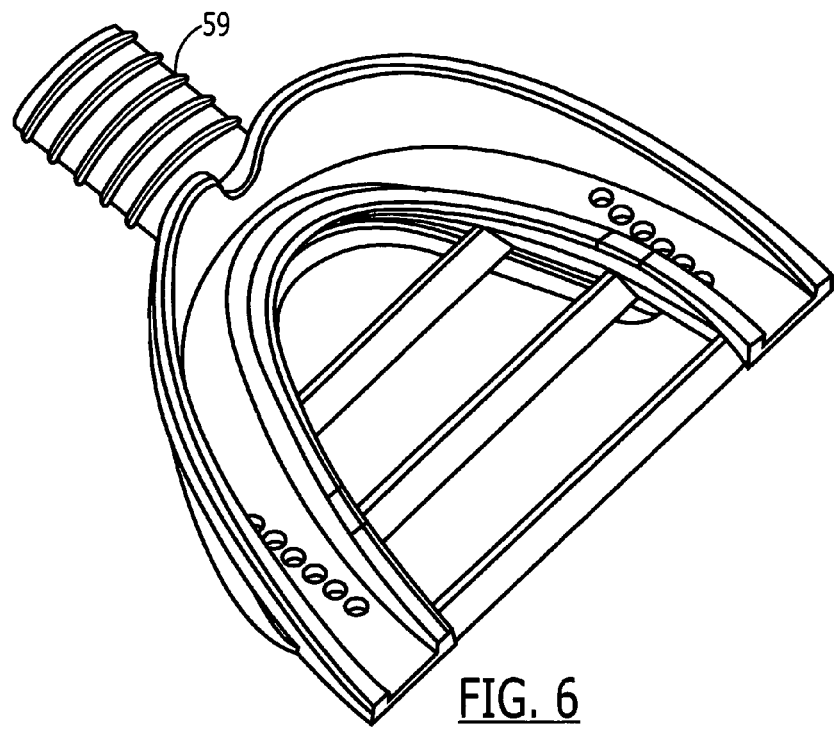
FIG. 6 is a perspective view of another embodiment of an adjustable dental device illustrating a different connection means.

Turning to FIG. 6, a perspective view of an adjustable dental device illustrating a different connection means is provided. In place of the dental device connector illustrated in FIG. 1 and the alternative nut-and-bolt connection means illustrated in FIGS. 2-5, a compression fit member 59 is used. The member includes a plurality of ridges used to hold member 59 within a corresponding aperture as will be illustrated in subsequent figures. Compression fit member 59 may be made of a plastic material, but should retain its shape when the dental device is heated for a custom fit. This can be accomplished through use of the same material as the bite blocks but with greater thickness and mass or by using a different material for compression fit member 59.

Figure 7:
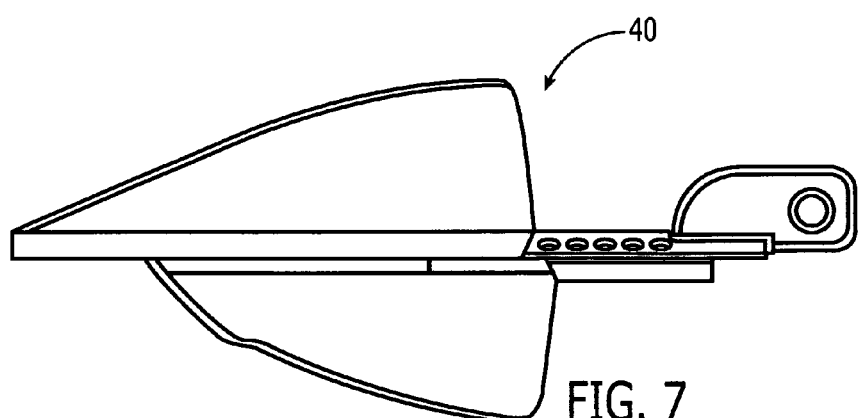
FIGS. 7 and 8 are side elevations of an adjustable dental device illustrating the range of adjustability for malocclusion.
Figure 8:
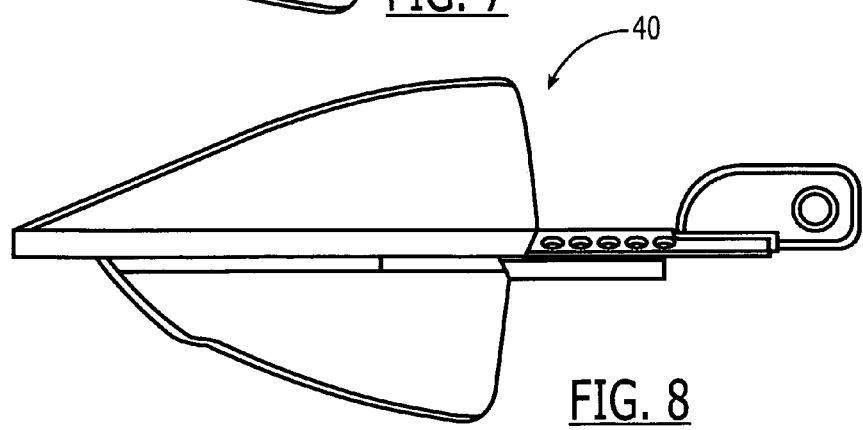

Turning to FIGS. 7-8, side elevation views of adjustable dental device 40 are provided to illustrate the underbite and overbite adjustability, respectively, of the device in accordance with the teachings of the present invention.

Having described an adjustable dental device 40 in accordance with the teachings of the present invention, attention is now turned to how the device can be used with a wide range of CPAC devices and respirators.

FIG. 9 illustrates an embodiment of the present invention in which adjustable dental device 40 is attached to a respirator having nasal inserts 66, 68, head strap attachments 70, 72 and air hose 74. The particular interface or respirator illustrated in FIG. 9 is sold under the product name OPTILIFE RESPIRONICS, but represents a number of CPAC interface products having nasal inserts and head straps. As illustrated here, dental device mount 76 provides an attachment means to connect dental device 40 to this type of respirator.

FIG. 10 illustrates further details of dental device mount 76 in a perspective view. Mouthpiece mount 76 includes bracket 78 with, in this example, four vertically aligned holes through which adjustable dental device 40 may be connected using the nut-and-bolt connection described above or an equivalent connection means. Clip 80 therefore provides a means to secured dental device mount 76 to air hose 74 (shown in FIG. 9). Clip 80 as illustrated in this embodiment is a plastic, snap-ring type fastener. It may include open ends 87, 89, which are curled so as to allow for the placement of a rubber band or the like to provide additional compression to the clips when mounted around air tube 74.

The extension of bracket 78 beyond the upper plane formed by clip 80 allows for the clearance needed to position dental device 40 at the proper distance from nasal inserts 66, 68 (as shown in FIG. 9) for a particular patient while clearing or otherwise not interfering with strap attachments 70, 72 (also as shown in FIG. 9). In this way, dental device 40 of the present invention can be used with a wide range of respirators.

Turning to FIG. 11, an alternative dental device mount 82 having upper clip 84 and lower clip 86 is illustrated. This embodiment of mount 82 provides additional fastening strength and rigidity as may be desired by some patients and with certain air tubes or respirators. As with the single clip embodiment, dental device mount 82 is a plastic, snap-ring type fastener or equivalent. Both or either clips may include open ends, which are curled so as to allow for the placement of a rubber band or the like to provide additional compression to the clips when mounted around air tube 74 (shown in FIG. 9).

Figure 12:
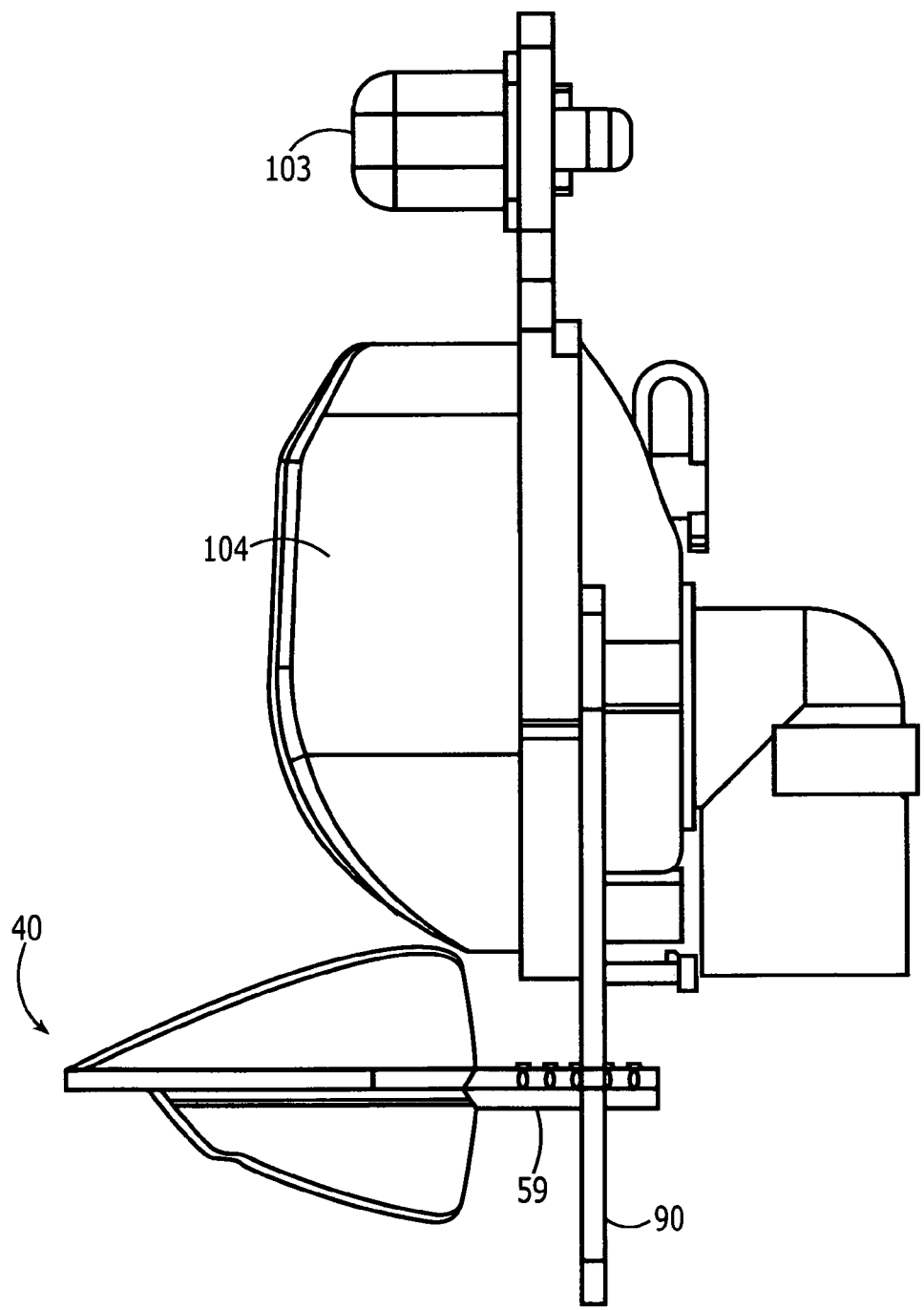
FIG. 12 is a side elevation view illustrating a dental device mount for attaching an adjustable dental device to a respiratory having a nasal mask.

FIG. 12 illustrates another embodiment of the present invention in which adjustable dental device 40 is attached to a nasal mask type respirator 104. Nasal mask dental device mount 90 has a substantially U-shaped body as illustrated in subsequent figures and includes a plurality of attachment clips which are illustrated and explained below. The particular respirator illustrated here includes a forehead rest 103 in addition to the nasal mask 104. The nasal mask dental device mount 90 can be used with or without a forehead rest 103.

Figure 13:
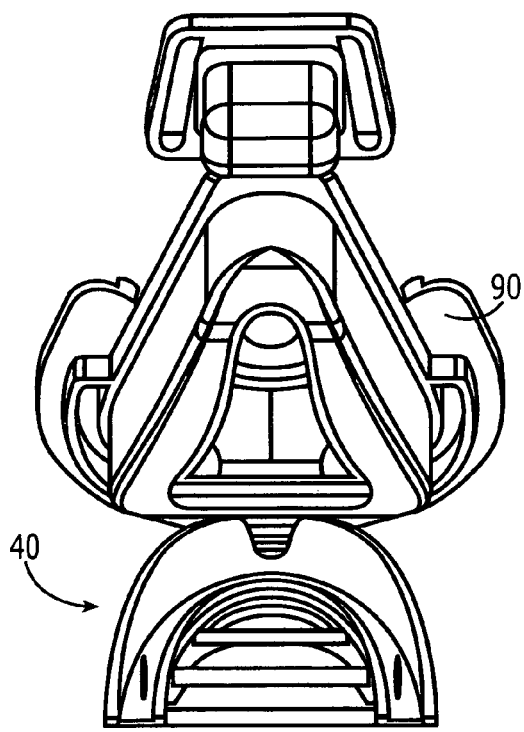
FIG. 13 illustrates further details of the dental device embodiment shown in FIG. 12 for use with a nasal mask type respirator.

Turning to FIG. 13, dental device 40 is illustrated attached to dental device mount 90 for use with a nasal mask type respirator. The substantially U-shaped body of mouthpiece mount 90 generally conforms to the shape of the nasal mask which provides for a secure connection. Dental device mount 90 is preferably made of plastic and is substantially rigid, however, other materials can be used including metal and composites.

Figure 14:
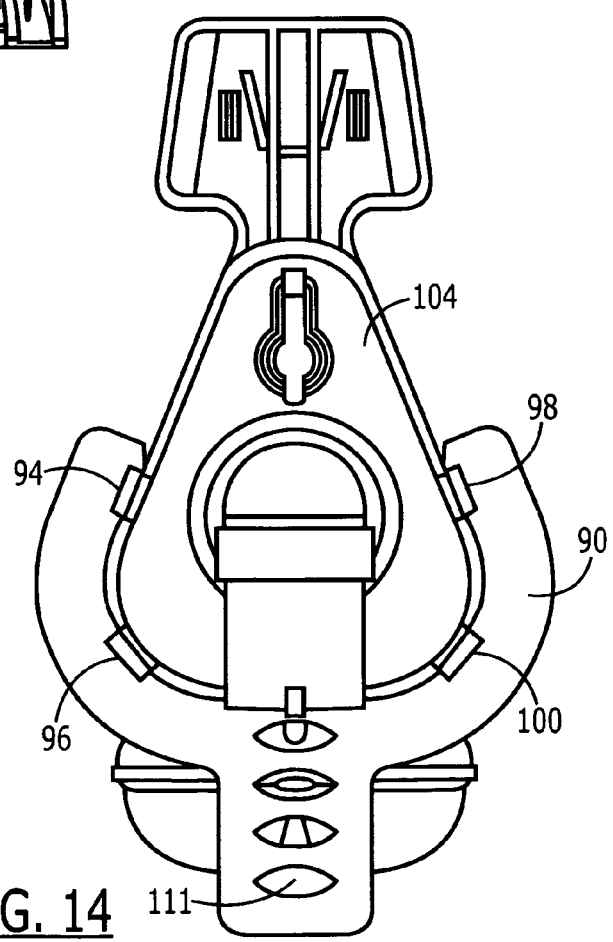
FIG. 14 is a rear elevation view of the dental device embodiment shown in FIG. 12 illustrating further details of a dental device mount for use with a nasal mask type respirator.

FIG. 14 illustrates further details of dental device mount 90. Mouthpiece mount 90 includes clips 94, 96, 98, 100 for engaging and securing mount 90 to nasal mask 104. A different number of clips may be used for securing mount 90 to nasal mask 104, preferably in a symmetrical distribution for balance of forces. Mounting bracket 90 includes, in this illustration, four vertically align holes 111 through which compression fit member 59 may be inserted and secured therein. The substantially U-shaped body of mouthpiece mount 90 and its fit to the shape of nasal mask 104 is clearly illustrated here.

Figure 15:
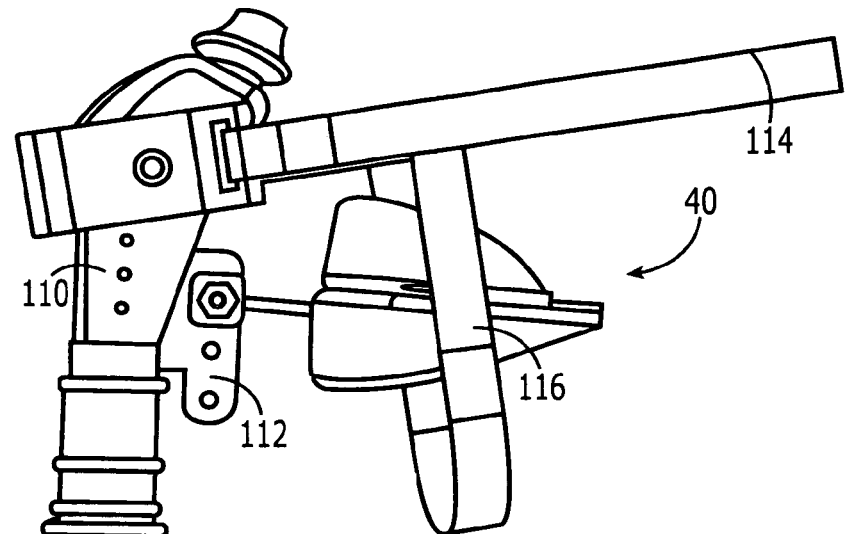
FIG. 15 is a perspective view illustrating another embodiment of the present invention which includes an alternative interaction assembly having an integral mounting bracket.
Figure 16:
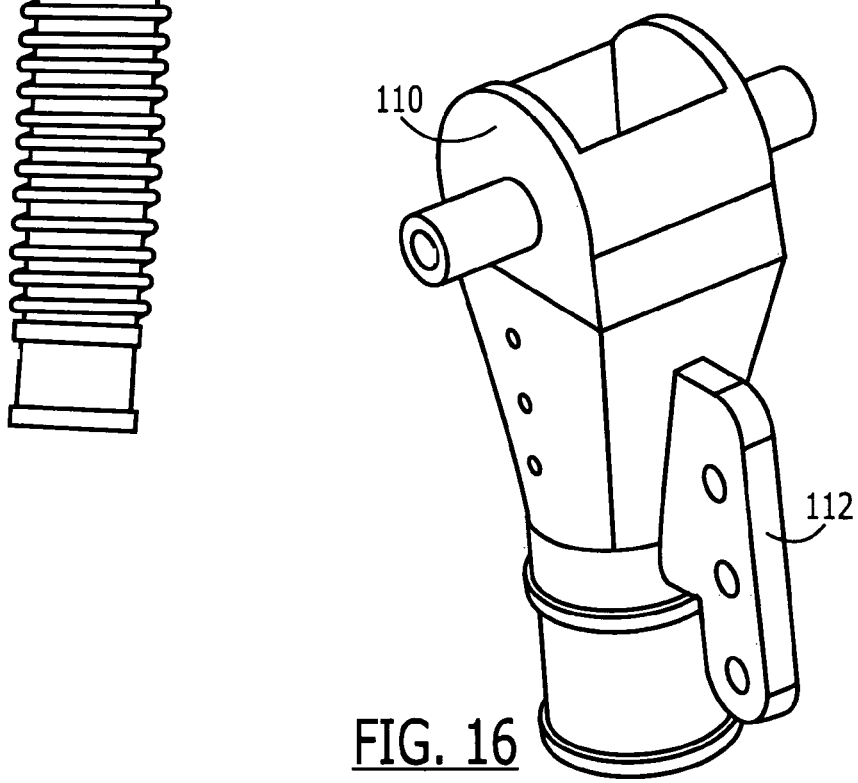
FIG. 16 illustrates certain details of the alternative interaction assembly having an integral mounting bracket.

FIGS. 15-16 illustrate another embodiment of the present invention in which adjustable dental device 40 is attached to an alternative CPAP interaction assembly 110 having integral mounting bracket 112, head strap 114, and chin strap 116. As with the previous illustrations, adjustable dental device 40 may be connected to this type of alternative interaction assembly 110 using a nut-and-bolt connection or other connection means.

The present invention as taught above is readily adaptable to a wide range of CPAP devices and respirators, and can be used with various types of nasal inserts, nasal masks, and interfaces. The dental device as taught herein, restrains the tongue from obstructing the airway, encourages nasal breathing, and prevents teeth grinding. The adjustability of the orientation and distance of the dental device from the nasal inserts or nasal mask as taught above provides for a wide range of adjustability to accommodate differences in face shape and size. Furthermore, the adjustability of upper bite block and lower bite block prior to molding provides for a wide range of adjustability to accommodate differences in occlusion.

While only certain preferred embodiments of this invention have been shown and described by way of illustration, it is apparent to those skilled in the art that many modifications can occur to accommodate alternate versions. By way of example, based on the design of a particular CPAP device or respirator—whether of the nasal insert type, nasal mask type, or other type—alternate embodiments of the attachment means could be provided within the scope of this invention. Similarly, different means of adjustably attaching the bite blocks may be employed. Accordingly, these and other embodiments of the invention fall within the scope of the following claims.

What is claimed is:

1. An adjustable dental device for use with a CPAP system in the treatment of sleep apnea and snoring, comprising:
    an upper bite block;
    a lower bite block having one or more tongue retainers wherein said one or more tongue retainers comprise a substantially elongated member having a substantially triangular cross section wherein the two ends of said elongated member are attached to said lower bite block;
    means for adjustably connecting said upper bite block to said lower bite block; and
    means for connecting said dental device to a CPAP system.

2. The device as recited in claim 1 wherein said means for adjustably connecting said upper bite block to said lower bite block comprises a dovetail connection.

3. The device as recited in claim 1 wherein said means for adjustably connecting said upper bite block to said lower bite block comprises a peg connection.

4. The device as recited in claim 1 wherein said upper bite block and said lower bite block are comprised of a deformable material for forming a custom fit.

5. The device as recited in claim 4 wherein said means for connecting the dental device to a CPAP system comprises an attachment member having a first end attached to said dental device.

* * * * *